US00PP18095P2

(12) United States Plant Patent
Pieters

(10) Patent No.: US PP18,095 P2
(45) Date of Patent: Sep. 25, 2007

(54) ***CHRYSANTHEMUM* PLANT NAMED 'PPP COMP OR05'**

(50) Latin Name: *Chrysanthemum morifolium*
Varietal Denomination: PPP COMP OR05

(75) Inventor: Dirk Pieters, Oostnieuwkerke (BE)

(73) Assignee: Pieters Plant Production, Oostnieuwkerke (BE)

( * ) Notice: Subject to any disclaimer, the term of this patent is extended or adjusted under 35 U.S.C. 154(b) by 0 days.

(21) Appl. No.: 11/414,912

(22) Filed: Apr. 29, 2006

(51) Int. Cl.
*A01H 5/00* (2006.01)

(52) U.S. Cl. ..... Plt./290

(58) Field of Classification Search ..... Plt./290, Plt./287

See application file for complete search history.

*Primary Examiner*—Kent Bell
*Assistant Examiner*—June Hwu

(57) ABSTRACT

A new and distinct *Chrysanthemum* plant cultivar is disclosed, characterized by large decorative type inflorescences, consistent flowering response to short days, blooming consistently after 49 days of short day length, pale orange ray florets, free branching habit, and a consistent natural season flowering habit during the first week of September.

1 Drawing Sheet

Latin name of the genus and species: *Chrysanthemum morifolium.*
Variety denomination: 'PPP COMP OR05'.

BACKGROUND OF THE INVENTION

The new cultivar 'PPP COMP OR05' is a product of a cross between the female parent 'GEDI VL8' (U.S. Plant Pat. No. 11,344) and the male parent 'GEDI TWO LUC' (U.S. Plant Pat. No. 14,429). The new cultivar was discovered and selected by Dirk Pieters in September of 2003 in Oostnieuwkerke, Belgium.

Asexual reproduction of the new cultivar 'PPP COMP OR05' by terminal cuttings and tissue culture was performed in Oostnieuwkerke, Belgium and Oxnard, Calif., and has shown that the unique features of this new cultivar are stable and reproduced true to type on successive generations.

SUMMARY OF THE INVENTION

The cultivar 'PPP COMP OR05' has not been observed under all possible environmental conditions. The phenotype may vary somewhat with variations in environment such as temperature, daylength, and light intensity, without, however, any variance in genotype.

The following traits have been repeatedly observed and are determined to be the unique characteristics of 'PPP COMP OR05.' These characteristics in combination distinguish 'PPP COMP OR05' as a new and distinct *Chrysanthemum* cultivar:

1. Large pale orange inflorescences;
2. Consistent flowering response to short days, blooming consistently after 49 days of short day length;
3. Free branching habit; and
4. Consistent natural season flowering habit during the first week of September.

Plants of the new cultivar 'PPP COMP OR05' are similar to plants of the female parent variety, 'GEDI VL8' in most horticultural characteristics, however plants of the new cultivar 'PPP COMP OR05' are taller and wider. Also, the new cultivar 'PPP COMP OR05' has more inflorescences per lateral branch. Finally, 'PPP COMP OR05' has lighter orange ray florets and more yellow-orange disc florets than the bright yellow disc florets of the female parent 'GEDI VL8.'

Plants of the new cultivar 'PPP COMP OR05' are similar to plants of the male parent variety, 'GEDI TWO LUC' in most horticultural characteristics, however plants of the new cultivar 'PPP COMP OR05' are taller and wider. Also, the new cultivar 'PPP COMP OR05' has a bigger inflorescence diameter and more inflorescences per lateral branch. Additionally, 'PPP COMP OR05' has more yellow-orange ray florets compared to the greyed-orange ray florets of the male parent. Finally, the disc florets of 'PPP COMP OR05' are mostly visible in comparison to the non-visible disc florets of the male parent.

In comparison to the commercially available variety 'GEDI THREE PORA' (U.S. Plant Pat. No. 17,067), 'PPP COMP OR05' has a wider plant spread. Additionally, the new variety 'PPP COMP OR05' has a longer inflorescence longevity. Further, the new variety 'PPP COMP OR05' has more inflorescences per lateral branch and more ray florets per inflorescence.

BRIEF DESCRIPTION OF THE PHOTOGRAPH

The accompanying photograph in FIG. 1 illustrates in full color a typical plant of 'PPP COMP OR05' grown in a 2 gallon container. One cutting was used in the pot, planted mid May and grown under outdoor field conditions. The colors are as nearly true as is reasonably possible in a color representation of this type.

DETAILED BOTANICAL DESCRIPTION

In the following description, color references are made to The Royal Horticultural Society Colour Chart except where general terms of ordinary dictionary significance are used. The following observations and measurements describe 'PPP COMP OR05' plants grown in Oxnard, Ventura County, Calif., during the months of May through September 2005. The growing temperature ranged from 12° C. to 15° C. at night to 12° C. to 20° C. during the day. Measurements and numerical values represent averages of typical flowering types.

Botanical classification: *Chrysanthemum morifolium* cultivar 'PPP COMP OR05.'
Commercial classification: Garden-type *Chrysanthemum*.

PROPAGATION

Time to rooting: 7 to 14 days at approximately 21° C.
Root description: Fine, fibrous.

PLANT

Growth habit: Mounding herbaceous perennial.
Height: Approximately 30 cm.
Plant spread: Approximately 59 cm.
Growth rate: Moderate.
Branching characteristics: Free Branching.
Length of lateral branches: Approximately 26 cm.
Number of leaves per lateral branch: Approximately 28.
Age of plant described: Approximately 120 days.

FOLIAGE

Leaf:
*Arrangement.*—Alternate single.
*Average length.*—Approximately 5.9 cm.
*Average width.*—Approximately 4 cm.
*Shape of blade.*—Ovate.
*Apex.*—Acuminate.
*Base.*—Attenuate.
*Attachment.*—Stalked.
*Margin.*—Serrate.
*Texture of top surface.*—Lightly pubescent.
*Texture of bottom surface.*—Lightly pubescent.
*Leaf internode length.*—Approximately 2 cm.
*Color.*—Young foliage upper side: Near Green 137A. Young foliage under side: Near Green 138B. Mature foliage upper side: Near Green 137A. Mature foliage under side: Near Green 138B.
*Venation.*—Type: Palmately net. Venation color upper side: Near Green 138C. Venation color under side: Near Green 138C.

Petiole:
*Average length.*—Approximately 2.5 cm.
*Color.*—Near Green 138C.
*Diameter.*—Approximately 0.1 cm.

BLOOM

Inflorescence:
*Flowering habit.*—Induced by darkness period greater than 13.5 hours, approximately 49 days of approximately day length required to induce and develop blooms.
*Inflorescence form.*—Decorative.
*Natural flowering season.*—Approximately first week in September.
*Number of inflorescences per lateral branch.*—Approximately 35.
*Inflorescence diameter.*—Approximately 5.3 cm.
*Inflorescence depth.*—Approximately 2 cm.
*Inflorescence longevity on plant.*—Approximately 28 to 32 days.
*Persistence.*—Persistent.

Ray florets:
*Appearance.*—Matte.
*Texture.*—Smooth.
*Average number of ray florets per inflorescence.*—205.
*Shape.*—Oblanceolate.
*Aspect.*—Flat.
*Margin.*—Entire.
*Apex.*—Obtuse.
*Length.*—Approximately 2 cm.
*Width.*—Approximately 0.5 cm.
*Color.*—Upper surface at first opening: Near Orange-Red 31A. Upper surface at maturity: Near Yellow-Orange 21A. Upper surface at fading: Near Yellow-Orange 16A. Under surface at first opening: Near Orange-Red 31B. Under surface at maturity: Near Yellow-Orange 14C. Under surface at fading: Near Yellow 12B.

Disc florets:
*Appearance.*—Shiny.
*Texture.*—Smooth.
*Average number of florets per disc.*—Approximately 45.
*Shape.*—Cylindric.
*Apex.*—Obtuse.
*Average length.*—Approximately 0.5 cm.
*Average width.*—Approximately 0.1 cm.
*Color.*—At first opening: Near Yellow 9A. At maturity: Near Yellow-Orange 14A. At fading: Near Yellow 12A.

Peduncle:
*Length.*—At terminal end (shortest): Approximately 4 cm. At lateral end (longest): Approximately 7 cm.
*Angle to stem.*—Acute.
*Strength.*—Moderate.
*Color.*—Near Green 138B.
*Habit.*—Upright.
*Diameter.*—Approximately 0.1 cm.
*Surface texture.*—Lightly pubescent.

Inflorescence bud:
*Length.*—Approximately 0.5 cm.
*Diameter.*—Approximately 0.5 cm.
*Form.*—Globular.
*Color.*—Near Yellow-Green 145A.

Involucral bracts (phyllaries):
*Appearance.*—Matte.
*Texture.*—Lightly pubescent.
*Number.*—Approximately 20.
*Shape.*—Ovate.
*Margin.*—Entire.
*Apex.*—Acute.
*Length.*—Approximately 0.4 cm.
*Width.*—Approximately 0.3 cm.
*Color.*—Upper side: Near Green 138A. Under side: Near Green 138B.

REPRODUCTIVE ORGANS

Ray florets:
*Number of pistils per floret.*—1.
*Stigma shape.*—2 branched.
*Stigma color.*—Near Yellow 9A.
*Style color.*—Near Green-Yellow 1A.
*Style length.*—Approximately 0.2 cm.
*Stamens.*—Absent.

Disc florets:
*Number of pistils per floret.*—1.
*Stigma shape.*—Cylindric.

*Stigma color.*—Near Yellow-Orange 14A.
*Style length.*—Approximately 0.1 cm.
*Style color.*—Near Yellow-Green 154D.
*Number of stamens per floret.*—Approximately 5.
*Anther shape.*—Tubular.
*Anther color.*—Near Yellow-Orange 14A.
*Pollen color.*—Near Yellow-Orange 14A.

OTHER CHARACTERISTICS

Disease resistance: Neither resistance nor susceptibility to diseases or pests has been observed in this variety.

Drought tolerance/cold tolerance: Flowering plants are hardy to low temperatures about −2° C. Non-flowering plants are hardy in the approximate range of 3° C. to −6° C., depending upon duration of cold and amount of moisture in the soil. With adequate water plants are hardy to a high temperature of 45° C.

Fruit/seed production: Commercially, this plant is not used or observed in a stage where seeds would be produced. Therefore, seed production has not been observed.

What is claimed is:

1. A new and distinct cultivar of *Chrysanthemum* plant named 'PPP COMP OR05' as herein illustrated and described.

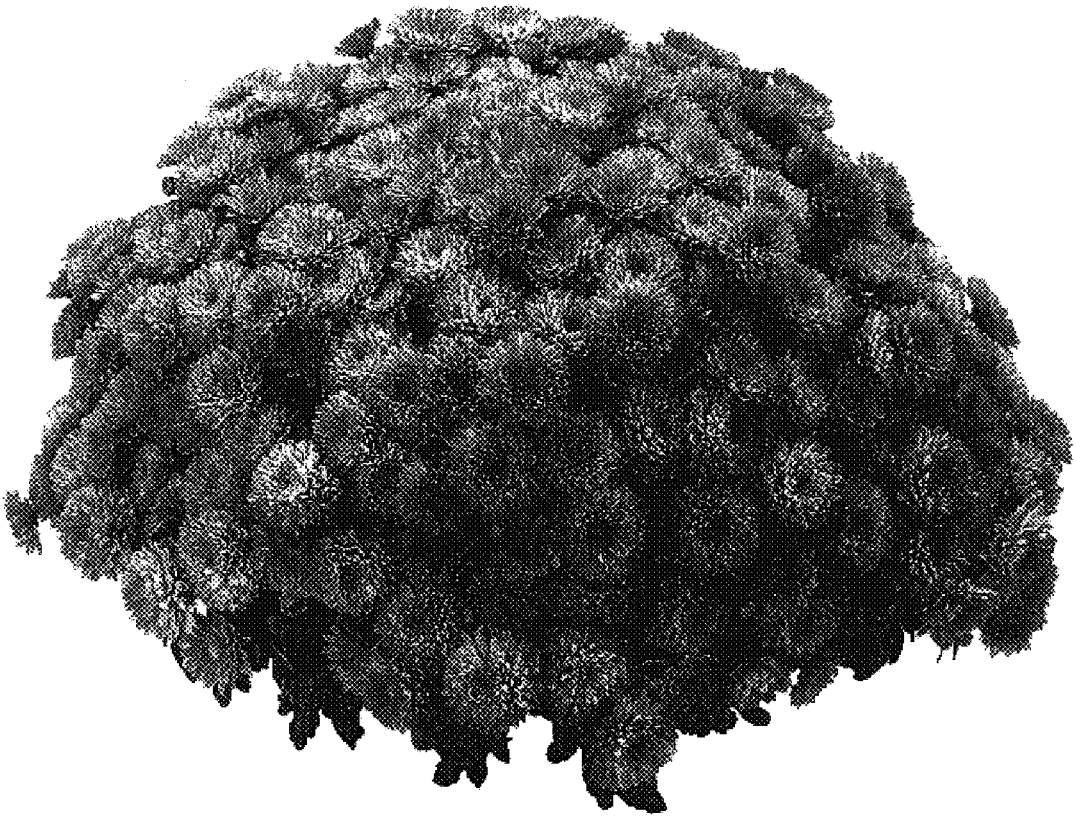

* * * * *